United States Patent [19]
Hamilton et al.

[11] 4,293,095
[45] Oct. 6, 1981

[54] AIR TREATING DEVICE

[75] Inventors: Peter W. Hamilton, Cincinnati; William P. Lewis, Westchester, both of Ohio

[73] Assignee: The Procter & Gamble Company, Cincinnati, Ohio

[21] Appl. No.: 93,090

[22] Filed: Nov. 9, 1979

[51] Int. Cl.³ .............................................. A61L 9/04
[52] U.S. Cl. ...................................... 239/35; 239/47; 116/200
[58] Field of Search ....................... 239/35, 44, 45, 49, 239/47, 50, 309, 313; 116/227, 264, 299

[56] References Cited

U.S. PATENT DOCUMENTS

| | | | |
|---|---|---|---|
| 64,548 | 1/1900 | Rose | 239/35 |
| 1,337,029 | 4/1920 | Weitzel | 222/390 X |
| 1,337,030 | 4/1920 | Weitzel | 222/390 X |
| 1,898,785 | 2/1933 | Murdoch et al. | 239/49 X |
| 2,521,181 | 9/1950 | Morse | 116/227 X |
| 2,636,644 | 4/1953 | Taylor | 222/90 |
| 2,671,424 | 3/1954 | Herring et al. | 116/227 X |
| 2,958,469 | 11/1960 | Shuster | 239/35 X |
| 3,250,122 | 5/1966 | Doering | 73/298 X |
| 3,254,841 | 6/1966 | De Loncker, Sr. | 239/45 |
| 3,420,205 | 1/1969 | Morison | 73/292 X |
| 3,587,968 | 6/1971 | Hennart et al. | 239/47 |
| 3,620,677 | 11/1971 | Morison | 252/425.5 X |
| 4,051,628 | 10/1977 | Knapp et al. | 239/35 X |
| 4,128,508 | 12/1978 | Munden | 252/522 |

Primary Examiner—Daniel M. Yasich
Attorney, Agent, or Firm—Richard C. Witte; Thomas H. O'Flaherty; John V. Gorman

[57] ABSTRACT

An air treating device in which the exhaustion of the operative fluid is visually signaled by a run-out signal system. The operative fluid and an immiscible signal fluid are held in a reservoir having associated therewith a substrate that selectively first wicks the operative fluid onto the evaporative surface portion of said substrate and, when the operative fluid is substantially depleted, the substrate then transports the signal fluid to the evaporative surface. The signal fluid is of a different hue from the operative fluid to provide an easily observed signal denoting exhaustion of the operative fluid.

8 Claims, 4 Drawing Figures

U.S. Patent  Oct. 6, 1981  4,293,095
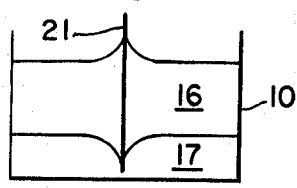
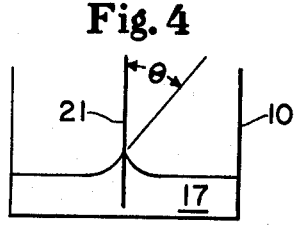
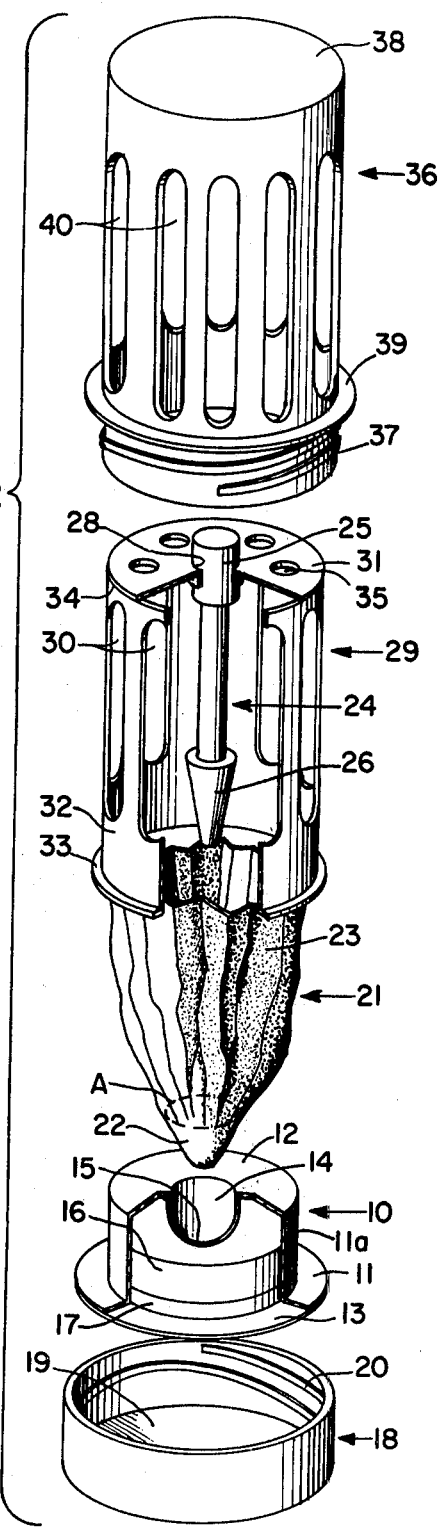

AIR TREATING DEVICE

TECHNICAL FIELD

The invention relates to air treating devices and, more particularly, to air treating devices with which an operative fluid is evaporated to effect the air treatment.

BACKGROUND ART

Air treating devices in which an operative fluid is evaporated to effect the air treatment have been in use for many years. One such device is disclosed in U.S. Pat. No. 3,587,968, which issued to C. Hennart et al. on June 28, 1971. In this patent a sealed reservoir houses the liquid to be evaporated. A destructible closure device interrupts communication between the interior of a wick tube and the atmosphere before use. To activate the device, means is provided to destroy the closure device.

One of the problems associated with such devices is that the consumer usually does not know when the operative fluid has been exhausted. Consequently, such devices are frequently maintained in use even though they are no longer effective and the consumer does not have the air treatment desired until the exhausted condition of the device is finally realized and the device is replaced with an operative substitute. The present invention provides a means for readily detecting visually that the operative fluid has been exhausted.

The use of run-out signal indicators is not new. Means for indicating exhaustion of a primary or operative fluid or material have been employed in a number of inventions. For example, U.S. Pat. Nos. 1,337,029 and 1,337,030, issued to P. R. Weitzel on Apr. 13, 1920 disclose a soap dispenser that employed two discrete layers of soap, one of which was intended to be expressed from the container last and to have a distinguishing characteristic, such as scent or color, to signal that the supply of soap is almost exhausted.

U.S. Pat. No. 2,636,644, issued to A. Taylor on Apr. 28, 1953, teaches the use of materials of different viscosity such that a high viscosity material, which is situated at the bottom of a collapsible tube in small quantity, causes a sudden increase in the force required to express the contents after the primary, or low viscosity material, is exhausted. A. Herring et al., U.S. Pat. No. 2,671,424, issued Mar. 9, 1954, relates to a pressurized dispenser in which the fluid pressure drop that occurs as the primary fluid is used, breaks a smaller, dye-bearing receptacle to indicate fluid depletion.

Knapp et al., U.S. Pat. No. 4,051,628, issued Oct. 4, 1977, discloses a container to dispense a hydrophilic gel into a growing medium. The gel contains a soluble dye that diffuses through the growing medium at a faster rate than the gel so that the growing medium changes (loses) color when the gel is nearly exhausted.

In Munden, U.S. Pat. No. 4,128,508, issued Dec. 5, 1978, a color change signal system is shown. The device employs two miscible fluids, one being a perfume and the other being either an acid or a base, and a substrate capable of transporting the fluids. The substrate is impregnated with a pH sensitive dye so that the acid or base, selected to volatize at a rate equal to that of the perfume, would, when depleted, cause a color change in the substrate thereby indicating depletion of the perfume. Assuming that the device will perform satisfactorily, it will be seen that there will be many constraints in the system design imposed by the miscibility, evaporation and pH properties of the fluids used.

It is an object of the present invention to provide an air treating device employing a color change system to signal exhaustion of the operative fluid, which system has different constraints than these systems presently known, in order to provide greater flexibility in the design and performance of such devices.

Another object of this invention is to provide an air treating device that is attractive in use, effective in performance, easy to operate and provides a visual signal based on highly controllable physical properties to connote exhaustion of the operative fluid.

DISCLOSURE OF THE INVENTION

This invention relates to an air treating device having an indicator system to signal exhaustion of the operative fluid. The device comprises a reservoir containing the operative fluid and a signal fluid having a hue different from that of the operative fluid. A substrate is associated with the reservoir that is capable of capillary transport of the operative fluid and the signal fluid from the reservoir to an evaporative surface portion of the substrate and is adapted to contact both fluids simultaneously in use. At least part of the substrate is visible when the air treating device is in its operative mode. The operative fluid and the signal fluid are immiscible and have relative surface tension properties which require that the substrate in use will selectively transport substantially all of the operative fluid toward the evaporative surface portion of the substrate prior to commencing transport of the signal fluid.

BRIEF DESCRIPTION OF THE DRAWINGS

FIG. 1 is an elevational view of the subject air treating device, partially broken away and sectioned, showing the general arrangement of the elements comprising a preferred embodiment in its activated and air treating mode.

FIG. 2 is an exploded perspective view of the air treating package of FIG. 1, partially broken away and sectioned for clarity, showing the individual elements comprising the device as they are prior to activation.

FIG. 3 is a schematic view of a test setup designed to screen substrates and signal fluids for prospective use in treating devices of the present invention and illustrating the menisci formed between the substrate and the operative and signal fluids.

FIG. 4 is a schematic view of a test setup similar to that of FIG. 3 and illustrating the meniscus formed between the substrate and the signal fluid, only, and the contact angles therebetween.

DETAILED DESCRIPTION OF THE INVENTION

While the specification concludes with claims particularly pointing out and distinctly claiming the subject matter regarded as forming the present invention, it is believed the invention will be better understood from the following details and description, which when taken in conjunction with the annexed drawings describes, discloses, illustrates and shows a preferred embodiment or modification of the present invention and what is presently considered and believed to be the best mode of practicing the principles thereof. Other embodiments or modifications may be suggested to those having the benefit of the teachings therein, and such other embodiments or modifications are intended to be reserved especially as they fall within the scope and spirit of the subjoined claims.

With reference now to the drawings, wherein like reference characters are utilized for like parts in the two figures, there is shown and illustrated in FIGS. 1 and 2 an easily operated air treating device that provides a run-out signal indicator for visually denoting that the operative fluid for air treatment is exhausted. The device comprises a lower cap 18 having telescoped therein a reservoir 10 containing the operative fluid 16 and the signal fluid 17; a substrate 21 of which the lower portion 22 is held in contact with the reservoir well 14 and the upper portion 23 is enclosed by the cage 29; a plunger rod 24 with a frustro-conically shaped lower end 26 adapted to hold the substrate portion 22 in the reservoir well 14 and pierce the material comprising the well 14 and a cylindrically shaped upper end 25 that is temporarily affixed within aperture 28 in the cage top 31; a cage 29 that provides slots 30 for air passage, and an outer cap 36 with slots 40 to act in conjunction with the cage slots 30 so as to provide a varying amount of air passage and with external threads 37 that mate with the internal threads 20 on the lower cap 18.

The device is initially assembled such that the reservoir is adhesively affixed to the interior of lower cap base 19, the cage 29, lower flange 33 is adhesively affixed to the reservoir flange and the upper end 25 of the plunger rod 24 is temporarily adhesively affixed in place in the aperture 28 of the cage top. The bottom of the outer cap 36 is threaded into the lower cap 18.

To activate the device the consumer removes outer cap 36 and presses down on the exposed portion of the plunger rod end 25 with sufficient force to break it loose from the aperture 28 and drive the lower plunger rod end 26 through the thin wall 15 of the reservoir well 14, thereby bringing the substrate 21 into contact with the reservoir fluids. The substrate will immediately begin transporting the operative fluid 16 to substrate portion 23. For greatest effect, the outer cap 36 need not be replaced in use. Usually however, since slower diffusion will be desired, the outer cap 36 is then rethreaded into the lower cap 18 and the consumer can position the slots 40 in relation to cage slots 30 so as to control the rate of evaporation and diffusion of the operative fluid into the atmosphere from the substrate portion 23. When the operative fluid is exhausted the substrate will then transport the signal fluid 17 to the substrate portion 23. Since the signal fluid is a different hue from the operative fluid, the consumer will know that the device is no longer providing air treatment.

Referring now to the individual parts comprising the subject device, each will be described with particularity, including approximate dimensions, illustrative materials of construction and the like, for an embodiment which is believed to be appropriately designed for use in treating the air in a room of average proportions. The reservoir 10 can comprise a disc-shaped bottom portion 13 that is preferably heat sealed to the flange 11 of a generally hat-shaped upper portion 11a, the crown of which can be 1.90 cm high with a 3.30 cm diameter. The topwall 12 of the crown has a centrally-located, approximately 9.5 mm diameter, 1.10 cm deep, recessed well 14 of a generally hemispherical or bullet-shape configuration projecting inwardly and downwardly and formed such that the bottommost surface 15 of the well 14 is highly frangible. For example, if the material comprising the upper portion 11a is thermoplastic, it can be heated and the well vacuum formed so that surface 15 is attentuated to a thickness of from about 0.05 to about 0.10 mm to reduce the force required to drive the plunger rod end 26 therethrough. As will be realized from subsequent description, the diameter of the well 14 should be only slightly larger than the aligned diameter of the plunger rod end 26 when it is in its lowest (activated) position, so the depth of the well 14 and the length and size of the plunger rod end 26 are appropriately selected to prevent gross spillage of the reservoir fluids when the air treating device is activated. The reservoir 10 is preferably constructed of thermoplastic materials capable of being thermoformed and heat sealed. For example, Barex 210 film, either transparent or opaque, of about 0.40 mm thickness has been found satisfactory but it can also be fabricated from other suitable materials that will not react or structurally deform in contact with the reservoir fluids.

The substrate 21 can be a fabric which is generally disc-shaped, of approximately 14.0 cm diameter, and is appropriately folded or otherwise shaped into an inverted, generally conical configuration to fit inside the cage 29. Following activation of the subject device, the substrate 21 is capable of selectively transporting (from lower portion 22 to upper portion 23 by capillary action) the operative fluid first and, when that is exhausted, of transporting the signal fluid. Appropriate substrates include non-woven fabrics, paper, woven fabrics, or any other materials which are capable of transporting the fluids 16 and 17 by capillary action and can be formed to serve as a wick in the context of the present invention. The manner of selecting a substrate for a particular use are more fully discussed later.

The lower portion 22 of the substrate 21 is tucked into the reservoir well 14 before activation of the air treating device and when the thinned down surface 15 of well 14 is pierced, the portion 22 is moved to a position at which it simultaneously contacts each of the reservoir fluids 16 and 17.

The remaining portion 23 of the substrate 21 is adapted to act as an evaporative surface for the transported operative fluid. The division of the substrate between these two portions 22 and 23 is roughly outlined and designated A. The division line A will vary depending on the depth to which the plunger rod 24 pushes the substrate into the reservoir 10.

The plunger rod 24 can be of generally cylindrical shape with an enlarged upper end which telescopes within aperture 28 in the cage top 31 of the cage 29. Lower end 26 is of an inverted, generally frustro-conical shape, which can be 1.75 cm long with a 9.0 mm upper diameter tapering to 3.2 mm diameter, and is designed to initially pierce the thinned-down surface 15 of the reservoir well 14 and, when forced to its lowest point, to act in conjunction with well 14 and the intervening substrate 21 to prevent gross spillage of the reservoir fluids 16 and 17.

The air treating cage 29 can be of two-piece construction, comprising an open-ended tube 32 and a disc-shaped cage top 31, affixed to one another along seam line 34 by adhesives or the like. The cage top 31 has a central aperture 28 adapted to receive the cylindrical plunger end 25 and a multiplicity of equally-spaced, circular, approximately 4.0 mm diameter bores 35 circularly arranged about aperture 28 to act as air passageways when the outer cap 36 is removed from the activated unit. If use of the subject device is contemplated only with the outer cap 36 applied, the bores 35 can be omitted from cage top 31. The generally cylindrical tube 32, which can be about 3.95 cm diameter and about 6.35 cm long, has a small, outwardly projecting, base flange 33 and ten equally-spaced, longitudinally extending slots 30, each of which can be approximately 6.5 mm wide by 4.30 cm long, intended to act as additional air passageways. In the preferred embodiment the tube 32 is injection molded polypropylene and the cage top 31 is thermoformed Barex 210 film, but both can be fabricated from other materials that will not react or structurally deform in the presence of the evaporating operative fluid or signal fluid.

The lower cap 18 is of a generally inverted cup shape, sized to accept the lower portions of reservoir 10 and cage 29, and has a closed bottom end 19. The sidewall of lower cap 18 has interior threads 20 formed thereon.

The outer cap 36, also of a generally cylindrical configuration, can be about 7.30 cm long, have a 4.35 cm diameter and about 1.6 mm thick walls so that the interior sidewall of the outer cap 36 forms a slip fit with the exterior sidewall of the cage 29. Further, outer cap 36 has a closed top portion 38 and its sidewall has 10 equally-spaced, longitudinally extending slots 40, each of which can be about 6.5 mm wide by 4.30 cm long to provide air passageways. The slots 40 are positioned so they can be placed in alignment with the slots 30 of cage 29 when the device is in its assembled, activated mode. An outwardly extending flange 39 is disposed between the slots 40 and exteriorly formed threads 37 on the lower extremity of outer cap 36, which flange is designed to serve as a lower stop when the threads 37 mate with the interior threads 20 on the lower cap 18. The outer cap 36 is desirably made of injection molded polypropylene but can be fabricated from various other materials that will not react or structurally deform in the presence of the evaporating operative fluid or the signal fluid. In operation the rate of evaporation and, hence, the amount of air treatment in the atmosphere can be controlled by the degree of alignment of slots 40 in the outer cap 36 with the slots 30 in the cage 29. In the full open position the slots can provide 27.5 cm$^2$ of open area.

The operative fluid 16 can be any air-treating or air-freshener agent, including all volatile liquid substances that can be diffused into the atmosphere by evaporation. Examples of such operative fluids 16 are insecticides, insect repellants, bactericides, deodorants and perfumes. The signal fluid 17 is of a distinctly different hue than that of the operative fluid and must be immiscible therewith. The fluids 16 and 17 must have surface tension properties which require the substrate employed in the package to first selectively transport the operative fluid to the evaporative surface portion 23 of the substrate and, when the operative fluid is exhausted, to then transport the signal fluid toward the evaporative surface portion 23. Thus, the substrate, which is visible to the consumer, will appear to undergo a color change due to the different hue of the signal fluid when the operative fluid is exhausted, indicating that replacement is necessary.

In addition, the relative densities of the reservoir fluids 16 and 17 when used in the described embodiment should be such that the signal fluid 17 will be situated below the operative fluid 16 when the subject device is upright. The volume of signal fluid used should be sufficient to cover the bottom of the reservoir, otherwise some operative fluid may become trapped to one side of the signal fluid and not be transported onto the substrate prior to the signal fluid. In the described embodiment approximately 3.0 grams of signal fluid 17 can be used. The amount of operative fluid 16 will vary depending on the desired life expectancy of the air treating device. The described embodiment can use 4.2–7.2 grams of operative fluid 16.

The signal fluid 17 to be used in the described embodiment with this chosen operative fluid 16 must be immiscible with respect to the operative fluid, have a higher specific gravity and be of a different hue in order to be visually observable. To select a signal fluid 17, then, one needs to test for immiscibility. Since operative fluids employed in many air treating devices are a mixture of complex chemical substances, selection of potentially immiscible signal fluids will be based initially on a knowledge and judgment within the province of one ordinarily skilled in the art. Thereafter, a simple test can be employed of placing the chosen operative fluid and the selected signal fluid(s) together in a beaker, shaking the beaker and then observing if the fluids separate in layers. At this point it can further be observed whether the signal fluid has the higher specific gravity. If the signal fluid also has a different hue from the chosen operative fluid then the signal fluid can be used in further testing. However, for either aesthetic purposes or simply because the signal fluid is a transparent liquid, the addition of a dye may be required. Selection of a dye soluble in the signal fluid and immiscible relative to the perfume mixture is also within the province of one ordinarily skilled in the art. The procedure for selection of the signal fluid 17 thereafter and for selection of an appropriate substrate requires that surface tension measurements and interfacial tension measurements be obtained for these candidate signal fluids. By way of definition, surface tension refers to the interface between a liquid and a gas or between a solid and a gas and interfacial tension refers to the interface between two liquids or between a liquid and a solid. The surface or interfacial tension can be viewed as a surface energy tending to reduce the area of the interface between two substances.

For this invention, the surface tension measurement for the operative fluid 16 at its interface with the atmosphere needs to be substantially lower than the corresponding surface tension measurement for the signal fluid 17 at its interface with the atmosphere. By taking the surface tension measurement of the immiscible candidate signal fluids and comparing the values obtained with the surface tension measurement for the chosen operative fluid 16 one can eliminate candidate signal fluids that will not function properly. The remaining candidate fluids can then be subjected to further tests to determine which is optimum. The surface tensions of the fluids can be measured using an instrument such as the Fisher Surface Tensionmat Model 21 (available from the Fisher Scientific Co., 5481 Creek Rd., Cincinnati, Ohio as catalog number 14-814) and following the manufacturer's instructional materials.

The interfacial tension measurement of particular interest in this invention is that between the substrate and the respective reservoir fluids to be selected. Since this interfacial tension measurement is difficult, if not impossible, to accurately measure directly, an alternate visual test can be used.

In the visual test, a dry strip of the prospective substrate is dipped into a transparent container holding the immiscible, and therefore layered operative fluid 16 and candidate signal fluid. The properly matched substrate and fluids will produce and must maintain throughout the expected life of the operative fluid an interfacial tension profile as depicted in FIG. 3. Additionally, if the same substrate either dry or pre-wet with the operative fluid is then dipped into a transparent container holding only the selected signal fluid then the interfacial tension profile should be as depicted in FIG. 4. Certain substrates may not transport the signal fluid when dry but will transport it if pre-wet with the operative fluid. In actual use the substrate will necessarily be pre-wet with the operative fluid prior to transporting the signal fluid. What these visually observed profiles indicate is the capability, or lack thereof, of the prospective substrate to transport by capillary action the operative fluid and the signal fluid in a desired order. Generally, the substrate is capable of capillary transport of any given fluid if the profile produced shows a contact angle θ, schematically defined in FIG. 4, of less than 90° between the fluid and the substrate.

In the visual test described above as depicted in FIG. 3, the operative fluid 16 is transportable by the substrate since the contact angle is less than 90° while the signal fluid is not. This test simulates the precise condition that should occur at the instant the air treating device of this invention is activated. The visual test described as depicted in FIG. 4 simulates that moment in time when the operative fluid has just been exhausted from the container. At that point a contact angle of less than 90° must be formed between the remaining signal fluid and the substrate so that the signal fluid is transportable.

In addition to the visual test, the process for selecting the appropriate substrate preferably includes measurement of contact angles. The visual test described above, as depicted in FIG. 3, would continue until the operative fluid was exhausted and the signal fluid had been transported onto the substrate as completely as possible. The resulting appearance of the substrate with the signal fluid would indicate which substrate(s) performed best. Since it is probable that several substrates would perform well, selection of the best substrate for the two fluids can be made by measuring the contact angle. The problem in trying to measure the contact angle, however, is that one needs a uniform and flat surface upon which to place a few drops of the fluid to be studied. The substrate materials capable of capillary action are generally either woven or non-woven materials that present a random surface. Any contact angle measurement on the substrate would provide only an apparent angle. However, many of the substrates studied for the purpose of constructing a preferred embodiment of this invention utilized binders to effect a fiber-to-fiber bond. As such, the contact angle measurement for the operative and signal fluids can be compared in terms of a given substrate by placing a few drops of the fluid to be studied on a uniform film of the binder material. Contact angles with binder materials can be measured by using an instrument such as the Contact Angle Goniometer Model A100 (available from the Rame-Hart Co., Inc., 43 Bloomfield Ave., Mountain Lakes, N.J. 07046) using the following procedure:

(1) Place three or four drops of the raw binder on a clear glass microscope slide plate.

(2) Using a second plate, sandwich the binder between the two and work back and forth until a uniform film with no air bubbles is obtained.

(3) Carefully separate the two plates leaving a thin, uniform coating and place in a laboratory oven at the temperature recommended by the binder manufacturer for curing. Completely cure the binder then remove from the oven and allow to cool to room temperature.

(4) Level the goniometer specimen stage according to the manufacturer's directions and place the coated slide plate on the stage with the coated side up.

(5) Place a droplet of the fluid of interest on the slide plate. Droplet size should be 2.50 μl using a Hamilton model PB 600 Dispenser syringe (available from Hamilton Co., P.O. Box 10030, Reno, Nev. 89510).

(6) Read the contact angle at 1 minute, 5 minutes and 15 minutes after drop placement. If the droplet spreads to a 0° contact angle prior to 15 minutes, note the time at which complete spreading occurred.

(7) A sample of the actual substrate may be substituted for the coated glass microscope slide. Use a 1"×2" sample of the substrate. The contact angle observed is an apparent angle rather than the actual contact angle.

The potential usefulness of this invention is limited only by the number of properly compatible fluids and substrates to effect this run-out signal indicator system. The following examples will further illustrate this invention. Since air treating devices are commonly designed to diffuse volatile perfumes into the atmosphere for air freshening, the examples chosen are suitable for air freshener devices.

All of the examples listed below were prepared and tested using the same procedures and equipment. A 4 dram glass vial was used for the tests and 2 grams of signal fluid and 0.5 grams of operative fluid were used in the vial. A 1"×7" strip of substrate was suspended in the vial and the test in each example continued until the operative fluid was exhausted and the signal fluid had wicked into the substrate as completely as possible.

EXAMPLE 1

OPERATIVE FLUID: 0.5 grams of representative perfume mixture was prepared from the components listed below. The mixture had a surface tension of 31.5 dynes/cm.

|  | % by wt. |
|---|---|
| Orange Terpenes | 28.3 |
| Lemon Terpenes | 10.0 |
| Terpinolene | 5.0 |
| Linalool | 10.0 |
| Linalyl Acetate | 10.0 |
| 2,6-Dimethyl Heptene-2-AL(7) | 1.0 |
| Allyl-Cyclohexene Propionate | 8.0 |
| Octyl Aldehyde | 0.2 |
| Decyl Aldehyde | 1.0 |
| Citral | 10.0 |
| Dihydromyrcenol | 9.0 |
| Lazandine | 3.0 |
| Methyl Nonyl Acetaldehyde | 3.0 |
| Peppermint | 0.5 |
| Cis-3-hexenyl acetate | 0.2 |
| Rose Oxide | 0.2 |
| Linalool Oxide | 0.2 |
| Linettel(*) | 0.2 |
| Nerol Oxide | 0.2 |
| TOTAL | 100.0 |

(*)Registered trademark, Linettel available from Naarden International, 919 Third Avenue, New York, N.Y. 10022

SIGNAL FLUID: 2.0 grams of a signal fluid which is made of deionized water containing 0.009% by weight of Food, Drug and Cosmetic dye-Green 3 (Food & Drug Administration classification), which dye is soluble in deionized water and immiscible with the foregoing perfume mixture. This signal fluid has a surface tension of 55.6 dynes/cm.

SUBSTRATE: Kendall style #479.32 non-woven fabric.

| (100% rayon fiber, 1.5 denier, basis weight 31 g/m² Binder system - E32 supplied by Rohm & Haas Manufactured by | Kendall Corp. 1 Federal St. Boston, Mass. 02110) | |
|---|---|---|
| | Perfume | Deionized H₂O with dye |
| Contact Angle | 0° | 0° |

RESULTS: In this example the substrate tested, Kendall style #479.32, produced the proper menisci as per FIG. 3 and FIG. 4. This substrate may begin transporting the signal fluid somewhat prematurely due to the fact that the contact angle measurement between this substrate's binder and the signal fluid was essentially the same as between the perfume and the binder. Hence, the substrate would just as readily transport either fluid such that when the perfume volume was sufficiently low the substrate would sometimes be in contact with only signal fluid and would transport it.

EXAMPLE 2

OPERATIVE FLUID: The perfume mixture of Example 1.

SIGNAL FLUID: The signal fluid of Example 1.

SUBSTRATE: Arkon style #0802184CC non-woven fabric.

| (100% rayon fiber, 1.5 denier, basis weight 46 g/m² Binder system - HA8 supplied by Rohm & Haas.) Manufactured by | Arkon Corp. 315 Pendleton Rd. Greenville, SC 29601 | |
|---|---|---|
| | Perfume | Deionized H₂O with dye |
| Contact Angle | 0° | 95° |

RESULTS: In this example the substrate tested, Arkon style #0802184CC, produced the proper menisci per FIGS. 3 and 4. The measured contact angle for this substrate and the signal fluid was slightly greater than 90° and the substrate transported the signal fluid poorly.

EXAMPLE 3

OPERATIVE FLUID: The perfume mixture of Example 1.

SIGNAL FLUID: The signal fluid of Example 1.

SUBSTRATE: Arkon Style #S0707147 non-woven fabric.

| (100% rayon fiber, 1.5 denier, basis weight 35 g/m² Binder system - TR653 supplied by Rohm & Haas Manufactured by | Arkon Corp. 315 Pendleton Rd. Greenville, SC 29601 | |
|---|---|---|
| | Perfume | Deionized H₂O with dye |
| Contact Angle | 0° | 85° |

RESULTS: In this example the substrate tested, Arkon sytle #S0707147, produced the proper menisci per FIGS. 3 and 4. The measured contact angle for this substrate and the signal fluid was slightly less than 90° and the signal fluid transported well but slowly. This substrate is the preferred one for use with the deionized H₂O.

EXAMPLE 4

OPERATIVE FLUID: The perfume mixture of Example 1.

SIGNAL FLUID: The signal fluid of Example 1.

SUBSTRATE: Asahi-Kasei style #N5041 non-woven fabric.

| (100% nylon spunbonded fiber, basis weight 35 g/m² Manufactured by | Asahi Chemical Ind., Co., Ltd. Osaka, Japan) | |
|---|---|---|
| | Perfume | Deionized H₂O with dye |
| Contact Angle | 0° | 130° 28° (if prewet substrate with perfume mixture) |

RESULTS: In this example the substrate tested, Asahi-Kasei style #N5041, produced the proper menisci per FIG. 3 and per FIG. 4 if the substrate was prewet with the operative fluid. This substrate is a spun-bonded material and requires no binder so that the contact angles indicated are apparent angles measured between a strip of substrate and the particular fluid. The substrate's contact angle with the signal fluid was greater than 90° unless the substrate was initially prewet with the operative fluid. The prewet substrate would then transport the signal fluid, but only so long as the operative fluid had not completely evaported. The final appearance of the substrate was splotchy as the signal fluid would not uniformly transport across the substrate.

EXAMPLE 5

OPERATIVE FLUID: The perfume mixture of Example 1.

SIGNAL FLUID: The signal fluid of Example 1.

SUBSTRATE: DuPont Sontara style #8023 non-woven fabric

| (100% polyester spunbonded fiber, Manufactured by | E.I. DuPont de Nemours Co., Inc. Sontara Process Group Old Hickory Plant Old Hickory, Tenn.) | |
|---|---|---|
| | Perfume | Deionized H₂O with dye |
| Contact Angle | 0° | 111° 0° (if prewet substrate with perfume |

-continued mixture)

RESULTS: In this example the substrate tested, DuPont Sontara style #8023, produced the proper menisci per FIG. 3 and per FIG. 4 if the substrate was prewet with the operative fluid. This substrate is a spunbonded material and requires no binder so the contact angles indicated are apparent angles measured between a stirp of the substrate and the particular fluid. The substrate's contact angle with the signal fluid was greater than 90° unless the substrate was initially prewet with the operative fluid. The prewet substrte would then transport the signal fluid, but only so long as the operative fluid had not completely evaporated. The final appearance of the substrate was splotchy as the signal fluid would not uniformly transport across the substrate. Additionally, this substrate has too great of an absorptive capacity making it impractical for use with a device employing relatively small amounts of operative fluid.

EXAMPLE 6

OPERATIVE FLUID: The perfume mixture of Example 1.
SIGNAL FLUID: 2.0 grams of a signal fluid is made of Ethylene Glycol. (Certified grade, available from Fisher Scientific Co., 5481 Creek Rd., Cincinnati, Ohio as cat. no E-178) containing 0.009% by weight of Food, Drug & Cosmetic dye Green 3 (Food & Drug Administration classification), which dye is soluble in the ethylene glycol and immiscible with the perfume mixture. This signal fluid has a surface tension of 51.2 dynes/cm.
SUBSTRATE: The non-woven fabric of Example 1.

|  | Perfume | Ethylene Glycol with dye |
|---|---|---|
| Contact angle | 0° | 0° |

RESULTS: In this example the substrate tested, Kendall style #479.32, produced the proper menisci per FIGS. 3 and 4. This substrate began transporting the signal fluid somewhat prematurely due to the fact that the contact angle measurement between this substrate's binder and the signal fluid was essentially the same as between the perfume and the binder. Hence, the substrate would just as readily transport either fluid such that when the perfume volume was sufficiently low the substrate would sometimes be in contact with only signal fluid and would transport it.

EXAMPLE 7

OPERATIVE FLUID: The perfume mixture of Example 1.
SIGNAL FLUID: The signal fluid of Example 6.
SUBSTRATE: The non-woven fabric of Example 2.

|  | Perfume | Ethylene Glycol with dye |
|---|---|---|
| Contact angle | 0° | 35° |

RESULTS: In this example the substrate tested, Arkon style #0802184CC, produced the proper menisci per FIGS. 3 and 4. The contact angle between this substrate's binder and the signal fluid was less than 90° and the substrate transported the signal fluid uniformly across the test strip.

EXAMPLE 8

OPERATIVE FLUID: The perfume mixture of Example 1.
SIGNAL FLUID: The signal fluid of Example 6.
SUBSTRATE: The non-woven fabric of Example 3.

|  | Perfume | Ethylene Glycol with dye |
|---|---|---|
| Contact angle | 0° | 30° |

RESULTS: In this example the substrate tested, Arkon style #S0707147, produced the proper menisci per FIGS. 3 and 4. The contact angle between this substrate's binder and the signal fluid was less than 90° and the substrate transported the signal fluid uniformly across the test strip. This substrate is the preferred one for use with the ethylene glycol and this combination of substrate and reservoir fluids is the preferred embodiment for this invention. Example 7 above is only slightly less preferred since its contact angle measurement for the substrate and signal fluid was greater and therefore that substrate would transport the signal fluid less readily.

EXAMPLE 9

OPERATIVE FLUID: The perfume mixture of Example 1.
SIGNAL FLUID: The signal fluid of Example 6.
SUBSTRATE: The non-woven fabric of Example 4.

|  | Perfume | Ethylene Glycol with dye |
|---|---|---|
| Contact angle | 0° | 0° |

RESULTS: In this example the substrate tested, Asahi Kasei style #N5041, produced the proper menisci per FIGS. 3 and 4. This substrate began transporting the signal fluid somewhat prematurely due to the fact that the contact angle measurement between this substrate's binder and the signal fluid was essentially the same as between the perfume and the binder. Hence, the substrate would just as readily transport either fluid such that when the perfume volume was sufficiently low the substrate would sometimes be in contact with only signal fluid and would transport it.

EXAMPLE 10

OPERATIVE FLUID: The perfume mixture of Example 1.
SIGNAL FLUID: The signal fluid of Example 6.
SUBSTRATE: The non-woven fabric of Example 5.

|  | Perfume | Ethylene Glycol with dye |
|---|---|---|
| Contact angle | 0° | 0° |

RESULTS: In this example the substrate tested, DuPont Sontara style #8023, produced the proper menisci per FIGS. 3 and 4. This substrate may begin transporting the signal fluid somewhat prematurely due to the fact that the contact angle measurement between this substrate's binder and the signal fluid was essentially the same as between the perfume and the binder. Hence, the substrate would just as readily transport either fluid such that when the perfume volume was sufficiently low the substrate would sometimes be in contact with only signal fluid and would transport it. Additionally, this substrate has too great of an absorptive capacity, making it impractical for use with a device employing relatively small amounts of operative fluid.

The perfume mixture described in the examples was selected to diffuse at a constant rate over time. Frequently perfume mixtures are composed of elements that evaporate at widely varying rates and hence, provide widely varying amounts of perfume for diffusion and air freshening. It was felt that if the perfume mixture was composed of elements with relatively close evaporation rates, i.e. selecting the perfume components to be within a narrow boiling point range, then the consumer would have available a relatively constant amount of perfume at all times for diffusion. This would tend to make the run-out signal device more credible and not appear to be either premature or tardy.

The signal fluids tested, deionized $H_2O$ and Ethylene Glycol, were chosen since they are relatively inexpensive and easily obtained. Other fluids could be tested and could conceivable perform equally well.

The substrates chosen are also those that were readily available and representative of non-woven sheet materials. The preferred embodiment would utilize a substrate that would first be capable of transporting both the operative fluid and the signal fluid; second, be capable of selectively transporting the operative fluid until it was depleted and of then transporting the signal fluid; and third, preferably be able to transport the fluid uniformly, especially the signal fluid, to avoid a splotchy appearance.

While the invention has been described, disclosed, illustrated and shown in terms of an embodiment or modification which it has assumed in practice, such other embodiments or modifications as may be suggested to those having the benefit of the teachings herein are intended to be expressly reserved, especially as they fall within the scope and breadth of the claims here appended.

What is claimed is:

1. An air treating device having an indicator system to signal exhaustion of the operative fluid therein, said device comprising a reservoir containing the operative fluid and a signal fluid having a hue different from that of the operative fluid, and a substrate that is capable of capillary transport of each of said fluids from said reservoir to an evaporative surface portion of said substrate and that is in contact with both fluids simultaneously in use, at least a part of said substrate being visible when the device is in its operative mode, said fluids being immiscible and having relative surface tension properties and interfacial tension properties which require that the substrate in use first selectively transport substantially all of the operative fluid toward said evaporative surface portion prior to commencing transport of said signal fluid.

2. The air treating device of claim 1 wherein said signal fluid has a density greater than that of said operative fluid.

3. The air treating device of claim 1 wherein said signal fluid has a contact angle with the substrate which is less than 90° and greater, when the substrate is prewet with operative fluid, than that of the operative fluid and substrate, whereby to permit transport of the signal fluid uniformly along the substrate following exhaustion of substantially all of said operative fluid.

4. The air treating device of claim 1 wherein said operative fluid is a perfume mixture.

5. The air treating device of claim 4 wherein said signal fluid is deionized water containing a soluble dye which is stable relative to the deionized water and the perfume mixture and is immiscible with the perfume mixture.

6. The air treating device of claim 4 wherein said signal fluid is Ethylene Glycol containing a soluble dye which is stable relative to the Ethylene Glycol and the perfume mixture and is immiscible with the perfume mixture.

7. The air treating device claim 1 wherein said operative fluid is selected from the group consisting of insecticides, insect repellants, bactericides and deodorants.

8. An air treating device having an indicator system to signal exhaustion of the operative fluid therein, said device comprising a sealed reservoir containing an operative fluid and an immiscible signal fluid of a hue different than that of the operative fluid, a plunger rod mounted above said reservoir and adapted to be moved downwardly, said reservoir having a frangible topwall portion in alignment with said plunger, a substrate intermediate said plunger rod and said frangible portion of said reservoir, said substrate being capable of capillary transport of each of said fluids and adapted to be moved downwardly with said plunger through said frangible portion and into simultaneous contact with said operative and signal fluids, said signal fluid having a substantially higher surface tension and density than the operative fluid and said signal fluid having a contact angle which is less than 90° with the substrate when the substrate is prewet with operative fluid, and which is greater than the contact angle of the operative fluid with the substrate, whereby said operative fluid will be selectively transported first by said substrate until it is substantially exhausted and then said signal fluid will be transported by said substrate to signal exhaustion of said operative fluid.

* * * * *